United States Patent
Dechev et al.

(10) Patent No.: US 8,000,792 B1
(45) Date of Patent: Aug. 16, 2011

(54) FAST-ACTING COUNTER-INCONTINENCE METHOD AND DEVICE

(76) Inventors: George D. Dechev, Pasadena, CA (US); Gueorgui G. Detchev, Los Angeles, CA (US); Roman D. Decheff, Pasadena, CA (US)

(*) Notice: Subject to any disclaimer, the term of this patent is extended or adjusted under 35 U.S.C. 154(b) by 361 days.

(21) Appl. No.: 12/431,567

(22) Filed: Apr. 28, 2009

Related U.S. Application Data

(63) Continuation-in-part of application No. 10/840,065, filed on May 6, 2004, now abandoned, which is a continuation-in-part of application No. 10/112,247, filed on Mar. 29, 2002, now abandoned.

(51) Int. Cl.
*A61N 1/18* (2006.01)
*A61N 1/24* (2006.01)

(52) U.S. Cl. .............. 607/41; 607/40; 607/58; 607/138; 607/143; 607/148

(58) Field of Classification Search .................... 607/40, 607/41, 58, 138, 143, 148
See application file for complete search history.

(56) References Cited

U.S. PATENT DOCUMENTS

| | | | |
|---|---|---|---|
| 2,874,695 A | 2/1959 | Vaniman | |
| 3,530,855 A | 9/1970 | Balding | |
| 3,810,140 A | 5/1974 | Finley | |
| 4,191,950 A | 3/1980 | Levin et al. | |
| 4,205,671 A | 6/1980 | Lassen | |
| 4,926,871 A | 5/1990 | Ganguly et al. | |
| 4,977,906 A | 12/1990 | DiScipio | |
| 5,036,859 A | 8/1991 | Brown | |
| 5,058,591 A | 10/1991 | Companion et al. | |
| 5,845,644 A | 12/1998 | Hughes et al. | |
| 6,097,297 A | 8/2000 | Fard | |
| 6,373,395 B1 | 4/2002 | Kimsey | |
| 6,407,308 B1 * | 6/2002 | Roe et al. | 604/361 |
| 6,570,053 B2 | 5/2003 | Roe et al. | |
| 6,573,837 B2 | 6/2003 | Bluteau | |
| 6,579,247 B1 | 6/2003 | Abromovitch et al. | |
| 6,579,274 B1 | 6/2003 | Morman et al. | |
| 2003/0011479 A1 | 1/2003 | Bluteau | |
| 2008/0300649 A1 * | 12/2008 | Gerber et al. | 607/41 |

FOREIGN PATENT DOCUMENTS

DK 97424 11/1963

* cited by examiner

*Primary Examiner* — Carl H Layno
*Assistant Examiner* — Natasha Patel
(74) *Attorney, Agent, or Firm* — Joseph E. Mueth

(57) ABSTRACT

A body-worn device for a fast healing of incontinence by building up the necessary durable behavioral conditioning, which provides the brain with the necessary proper control over the respective sphincters. The device is based on two different nerve mechanisms: a first electrical pulse stops the release of bodily wastes by a simple local reflex, arousing simultaneously the brain and preparing it to respond to a second, behavioral conditioning causing electric pulse, which follows within two seconds (i.e. still during the phasic period of the cortical learning process), strong enough to cause an unpleasant sensation, which the brain connects with the just begun incontinent release of bodily waste and acquires after only a few applications as a durable adversive behavioral conditioning. This shortens the healing period from many months to only a few days. The device is easily adjustable to the individual sensitivity of the involuntarily wetting or soiling person.

4 Claims, 2 Drawing Sheets

```
┌─────────────────────────────────────────┐
│   ATTACHING DEVICE 3 BY BELT 3a TO      │
│ THE LOWER PART OF THE PERSON'S ABDOMEN  │
│      BY HOOK AND LOOP FASTENER 3b       │
└─────────────────────────────────────────┘
                    ↓
┌─────────────────────────────────────────┐
│           TURNING ON DEVICE 3           │
│          BY ON/OFF SWITCH 4c            │
└─────────────────────────────────────────┘
                    ↓
┌─────────────────────────────────────────┐
│  ACTIVATING DEVICE 3 BY CLOSING ELECTRIC│
│   CIRCUIT ON THE END OF COUPLING 5b     │
│     CONNECTING MOISTURE DETECTOR 5      │
│          WITH ELECTRIC WIRE 5a          │
└─────────────────────────────────────────┘
                    ↓
┌─────────────────────────────────────────┐
│  GRADUALLY INCREASING THE STRENGTH OF   │
│   THE WETTING-STOPPING AND AROUSING     │
│  SIGNALS BY STRENGTH REGULATOR 4d ON    │
│   PLASTIC BOX 4 UNTIL THE PERSON        │
│ EXPERIENCES THE SENSATION OF A PINPRICK,│
│  WHICH ESTABLISHES THE PRE-SET SIGNALS  │
│         STRENGTH FOR THE PERSON         │
└─────────────────────────────────────────┘
```

FIG. 7

FAST-ACTING COUNTER-INCONTINENCE METHOD AND DEVICE

This application is a continuation-in-part of U.S. patent application Ser. No. 10/840,065, filed May 6, 2004 now abandoned, which was a continuation-in-part of U.S. patent application Ser. No. 10/112,247, filed Mar. 29, 2002 now abandoned, the disclosures of which are expressly incorporated herein by reference.

BACKGROUND OF INVENTION

The invention relates generally to methods and devices for treating involuntary incontinence. More particularly, it relates to treatments which act to rapidly program the brain to counteract incontinence, such as wetting and soiling.

The existing methods and devices for curing incontinence are based on the establishment of behavioral conditioning. However, the known devices and methods have a major shortcoming—a treatment period extending over three months to one year. Analysis shows that these methods and devices do not comply with a basic property of the learning process: the existence of two periods in the cortical response to novel stimuli—a short phasic period, of about two seconds, which occurs during and immediately after the presentation of a novel stimulus, and a more prolonged tonic period, which last several minutes. (Sebastian Peter Grossman, *A Textbook of Physiological Psychology*, page 644, John Wiley & Sons, Inc.) Behavioral conditioning established during the phasic response time is very durable and resistant to habituation, whereas a behavioral conditioning established during the tonic period habituates rapidly. (Habituation is a learning mechanism not to transfer or not to respond to sensory information).

Non-compliance with this basic property of the learning process causes the inadequacy of all existing methods and devices for curing the incontinence disorder which operate by audio, light or vibratory signals, as they do not arouse the brain sufficiently fast to the necessary degree to be able to connect the arousing signal with the incontinent release of bodily wastes during the phasic period. This is particularly the case with the patents and devices which use wired or radio transmitting devices to alert attendants at remote location, causing them to rush to wake up the wetting person. These signaling devices require many months to cure incontinence. From the studies of behavioral conditioning, it has been experimentally proven that even a well-established conditioned response cannot be elicited while the subject is asleep (Loucks, R. B., *J. Comp. Psychol.*, 25:415-426 (1938)). The signaling devices do not rouse the sleeping brain.

It has been proposed to apply an electric pulse to the human body. Such applications exist in Danish Patent No. 97424 and U.S. Pat. Nos. 3,870,051, 4,205,671, 6,407,308 B1 and 6,570,053 B2.

Danish Patent No. 97424 discloses an extremely high voltage of 400-900 volt with (column 2, line 17) an applied impulse of ultra short duration of 1/200 to 1/300 second (column 2, line 16) which, however, excludes the participation of the brain. The lack of application of consecutive electrical pulses fails to establish behavioral conditioning which is obligatory for achieving durable healing of the incontinence disorder.

U.S. Pat. No. 3,870,051 is based on an imposed urinary control by an externally located radio transmitter which operates a receiver and electrodes implanted in the body to the third and fourth, left and right sacral ventral motor nerve fibre roots (column 1, lines 27 to 29: column 5, lines 3 to 6) making possible a differential stimulation of the bladder and sphincter muscles. The operatively implanted electronic device which includes a power source, two radio receivers, a multivibrator and two electrodes is not created for the establishment of a behavioral conditioning, but for a permanent forced control operated by an external radio transmitter (column 2, line 66). If the device remains switched to a bladder hold mode, an outflow of urine will be prohibited, thereby adversely affecting the health of the patient. It is not by coincidence that the patent was developed on monkeys (baboons).

U.S. Pat. No. 4,205,671 to Lassen, et. al. employs a temperature sensor for a bed wetting device instead of one based on electrical contact. This prolongs the time between the onset of the wetting and the activation of the device as the temperature has to reach a predetermined level which exceeds the phasic period, optimal for the establishment of a durable behavioral conditioning. The device includes a timer circuit for a time delay control to delay the onset of the electrical pulse (column 5, lines 9 to 16). The pulse shock has a duration of less than 50 milliseconds "whereby the muscle of the bladder is closed as desired without the pulse attending the central nervous system. Thus, the patient or user will not feel the shock . . ." (column 5, lines 29 to 30). The failure to rouse the brain excludes the establishing of a behavioral conditioning.

U.S. Pat. Nos. 6,407,308 B1 and 6,570,053 B2 to Roe, et. al. are almost identical, using the same proactive sensor and differing only in that the second patent includes soiling. Adapted to contain, isolate and dispose of bodily wastes, both patents offer ways to predict their imminent release by using sensitive sensors and a receiver to detect the change of the electrical signals originating from the sphincters. An actuator supported by a controller performs a variety of responsive functions based mainly on a release of different substances. A responsive function of special interest to the present patent application is the release of electrical signals to the sphincter muscles. Aiming only to prevent an imminent release of bodily wastes, the electrical signals applied in U.S. Pat. No. 6,407,308 are described as follows: "While the maximum strength of the electrical impulse may be as high as about 35 Volts, the electrical impulse preferably has a voltage in the range of about 0.05 to about 5 Volts and more preferably in the range of about 0.3 to about 1 Volt . . ." (column 23, lines 39 to 43). The strength of the pulses of 5 volt can stimulate only a simple local anorectal reflex which represents a reflex arc completed only in the spinal cord as a segmental reflex, without the participation of the brain. The proof that all neural vents described in the Roe, et. al. patents are only on local and not on brain level comes from the acknowledgment, Roe '308 at column 23, lines 28 to 29, "This process may be alternatively referred to as dynamic graciloplasty nerve stimulation", as well as by the fact that in the Roe patents the brain is not mentioned.

Arousing the brain requires about ten times higher strength of the impulses than applied in the Roe, et. al. patents maximum of 35 volt. Therefore the Roe, et. al. device cannot achieve the arousing of the brain. Consequently, after failing to arouse the brain, a series of electrical pulses (Roe, et. al. '308, column 23, lines 38 to 56), together with the whole pulse train cannot cause the building up of the necessary behavioral conditioning, because the electrical pulses are too weak to arouse the brain, and lack the strength to cause an unpleasant reaction.

Another problem of these Roe, et. al. patents lies in the essence of the proactive sensor, which is the basis of the patent. Eliciting behavioral conditioning requires a starting event, which the brain can connect with the following "reward". In the case considered, this event is the incontinent release of bodily wastes. However, the Roe, et. al. proactive sensor is designed to anticipate the beginning of incontinent release of bodily wastes. Consequently, this basic property of the proactive sensor actually averts in principle the building up of a behavioral conditioning by the brain.

A discrepancy in these Roe, et. al. patents is the confusion which arises from the disclosure of just one EMG electrode (Roe '308, column 23, line 66; column 24, line 5; and column 28, line 17) for the application of electrical impulses delivered from the actuator to the human body. It is well known to those skilled in the art that an application of electrical pulses to the human body can be done by a pair of electrodes. Roe, et. al. do not disclose how the invention is practiced with a single electrode. This uncertainty is not solved even in the more recent Roe, et. al. patent, U.S. Pat. No. 6,570,053 B2 where it lacks any specification for a pair of electrodes. In addition, all electrodes 64, 65 and 66 on FIG. 1 are actually electromyographic measuring electrodes, which receive information on the entrance of the electrical circuit of the proactive sensor 60 and do not apply electrical pulses from the device to the human body.

Another significant problem with the Roe, et. al. proactive sensor, when it is receiving electrical signals emitted by the sphincter muscles, is that "The electrical activity measured by the surface electrodes includes a combination of EMG signals, other physiological signals present on the skin surface such as EKG and electro dermal activity, and environmental artifacts such as 60 Hz from electronic equipment or radio frequency interference." (Roe '308, column 26, lines 3 to 8). Applying bimodal electrodes in combination with a differential amplifier (Roe '308, column 26, lines 8 to 9) does, however, not avoid electrical signals caused by movements of the lower part of the wearer's body. Furthermore, it is recommended to increase or decrease the electrical activity, whereby for increases three preferred values are given—an increase about 2 times, 3 times and 5 times or more than the basal activity (Roe '308, column 27, lines 3 to 6). For the preferred decrease three preferred values are given, 50%, 75% and 95% (Roe '308, column 27, lines 17 to 20, and claims 7, 8 and 9). It is obvious that these values depend on the needs of the individual wearer.

These uncertainties in the nature of the different signals measured by the Roe, et. al. proactive sensor, as well as the singling out of their direction and optimal degree of change show that the adjustment to the individual wearer has to be made by a highly skilled specialist. Instead of this, the adjustment of the strength of the arousing and behavioral conditioning causing electrical signals of the present invention to the individual sensitivity of the incontinent person, is easy to perform and can be done by the wearer himself, for it is guided by the simple sensing of a feeling as by a pin prick.

The regulator of DiScipio U.S. Pat. No. 4,977,906 is constructed to program the kind and the intensity of visual, audio or tactile signals and not the strength of electrical pulses applied to the human body. The regulator of Roe, et. al. regulates the strength of electrical pulses delivered to the human body but only up to maximum of 30 volt, some ten times less than the strength necessary to arouse the brain and for an inducing of an adverse reaction, necessary to the establishment of behavioral conditioning. Therefore, any exchange of the regulators does not make a device able to build up behavioral conditioning and thereby heal incontinence disorders.

The detector from Brown U.S. Pat. No. 5,036,859 has one advantage over Roe, et. al.'s proactive sensor—that is reacting not before, but after the release of urine (column 4, line 63). Together with this, it has multiple disadvantages for an application on a device created to build up behavioral conditioning. Brown operates by ineffective arousing alarms (column 2, line 51; column 4, lines 41 to 42; column 4, line 67), an adsorbent sheet that delays the starting of the device (column 2, lines 31 to 32; column 8, line 47). Brown operates by remote signaling that delays further the arousing of the incontinent person's brain (column 4, line 67; column 5, lines 2 to 3). Brown is specially designed not for an immediate healing, but relies upon a long time training (column 9, lines 44 to 46). The very complicated electronics, which "includes a transmitter means for sending a coded digital signal" (Brown, column 2, lines 58 to 59) is justified only for an individual monitoring of many incontinent persons in day care centers, hospitals or nursing homes (Brown, column 2, line 44; column 5, lines 21 to 22). Consequently, the combination of the DiScipio or Roe, et. al. devices with the Brown sensor will not provide a device able to build up a behavioral conditioning, because the combined devices will have not only the flaws of the Brown sensor mentioned above, but will also not be able to send the electrical pulses to the human body, necessary for the building up of a behavioral conditioning due to the low voltage of the Roe, et. al. '308 patent, According to the present invention, the application of electrical pulses with appropriate strength in conformity with achievements of the physiology of learning and behavioral conditioning instead of audio, visual or vibratory arousing signals for arousing the brain, combined with an electrical signal for the building up of a behavioral conditioning makes it possible to shorten the healing period of the incontinent release of bodily wastes from many months to only a few days. The instantaneous cessation of the involuntary release eliminates the further worsening of the situation. The noiseless device worn on the body makes use possible during daytime and even in public places.

The main object of the present invention is to provide a fast-acting programming of the brain to counteract involuntary release of biological fluids by incontinent people.

Another object is to achieve this goal and yet to preserve the privacy of the person, so that it is possible to apply the invention in schools, camps and other public places for the curing not only of nighttime, but also of daytime, wetting and soiling.

Yet another object is to preserve the self-esteem of the involuntarily wetting or soiling person.

SUMMARY OF INVENTION

The device of the present invention comprises a body-worn belt attached to the lower abdomen of the human body. It includes a plastic box containing an on/off switch, a power source, a microprocessor electronics producing arousing and behavioral conditioning building up signals, and a regulator for their strength, further a pair of electrical signals applications units, and an exchangeable moisture detector, both connected with the plastic box by electrical wires. By sensing the moisture of the bodily wastes the device applies at least two consecutive electrical pulses following in a less than two seconds interval, each with a strength of 350 to 450 volt to the respective area of the human body, which drop to 40 to 80 volt when applied to the human body. These pulses operate on two nervous levels. The first signal causes an instant cessation of the involuntary release of waste by inducing a simple local anorectal reflex, stimulating a gamma efferent feedback loop, which involves only the fusimotor fibers from the polar regions of the intrafusal muscle spindles. This represents a reflex arc completed only in the spinal cord as a segmental reflex, without the participation of the brain. Simultaneously this first electrical pulse arouses the brain coinciding with the beginning of the incontinent release to the level of being able to build up a behavioral conditioning. A second electrical pulse, generated in less than two seconds after the first one, has the strength to address the already aroused brain and to induce an unpleasant sensation similar to a feeling as by a pin-prick. Coinciding with the phasic period of the learning time, this second electrical pulse stimulates a fast build up of a durable aversive behavioral conditioning to the incontinent release by linking the unpleasant feeling with the performance of the undesirable release of the bodily waste.

The method and device of the invention use a series of electric wetting-stopping and arousing signals pre-adjusted to the individual sensitivity of the person. This method makes it possible to build up the necessary reflex for the proper brain control of the bladder and anal sphincters after only a few applications.

The first electric signal of the series interrupts the wetting in a split second, thereby avoiding further embarrassment. Simultaneously it arouses the brain, preparing it to establish the reflex necessary for the proper control of the full bladder build up by the following signals.

The moisture detector consists of a foam body enclosing a separated pair of metal wires. When wetting occurs, the electrolytic urine closes the electrical circuit between the wires activating thereby the microprocessor electronics which releases the preset series or wetting-stopping and arousing signals which are applied to the human body by the pair of signals application units. The structure of the moisture detector varies with the recipient and location, being different for men, women and soiling. After each application, the now wetted moisture detector is exchanged by a dry moisture detector.

For proper functioning of the concept of the invention a pre-adjustment is carried out, unique to the individual recipient. Therefore, the electrical circuit is closed and the strength of the signal is gradually increased by its regulator until the recipient experiences the sensation of a pinprick. This then is the strength setting for the particular application. If necessary, the number of electrical signals can be increased by the regulator of their number. With these two settings the pre-adjustment of the device for the application to the particular patient is completed and the device is ready for duty.

DESCRIPTION OF THE DRAWINGS

FIG. 7 is a flowchart of the pre-adjustment of the fast-acting counter-incontinency device according to the individual sensitivity of the person.

DESCRIPTION OF THE PREFERRED EMBODIMENT

Turning to the drawings in greater detail.

Figure 1:
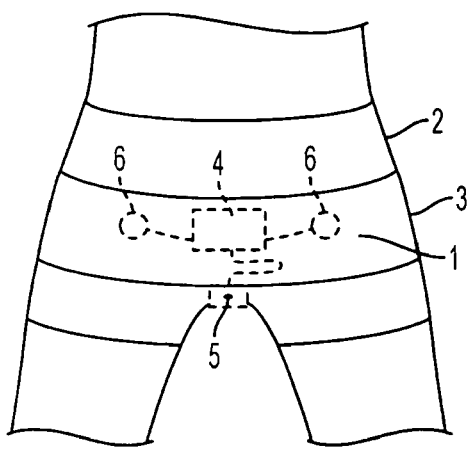
FIG. 1 is an overall view of a person's body with attached fast-acting counter-incontinence device.

FIG. 1 shows a person's body attached a fast-acting counter-incontinence device to the lower part of the person's abdomen 1, briefs, panties or diaper of the person, fast-acting counter-incontinence device 3, plastic box with power source and microprocessor electronics 4, exchangeable moisture detector 5, and pair of wetting-stopping and arousing signals application units 6.

Figure 2:
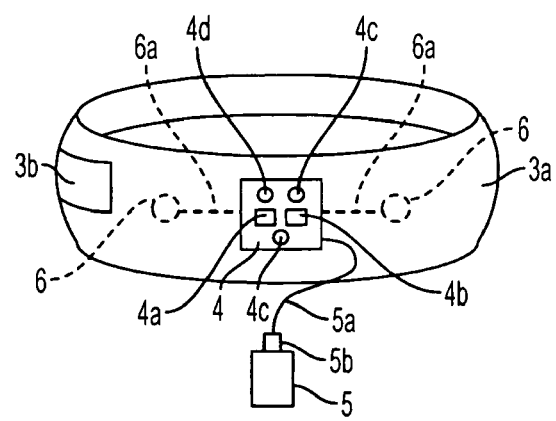
FIG. 2 is a detailed view of fast-acting counter-incontinence device.

FIG. 2 is a detailed view of fact-acting counter-incontinence device 3, belt 3a, hook-and-loop fastener 3b, plastic box with power source and microprocessor electronics 4, power source 4a, microprocessor electronics 4b, on/off switch 4c, regulator of strength of wetting-stopping and arousing signals 4d, regulator for pre-programming of the number of wetting-stopping and arousing signals 4e, exchangeable moisture detector 5, electric wire connecting the plastic box 4 with exchangeable moisture detector 5a, coupling 5b connecting exchangeable moisture detector 5 with electric wire 5a, pair of wetting-stopping and arousing signals applications units 6, pair of electric wires 6a connecting plastic box 4 with pair of wetting-stopping and arousing signals application units 6.

Figure 3:
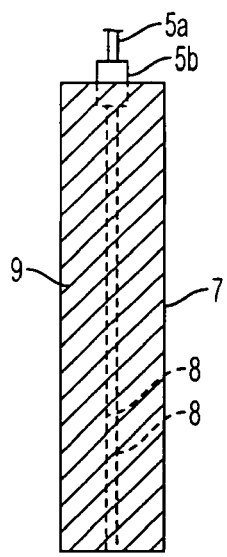
FIG. 3 is a detailed of view exchangeable moisture detector for women and soiling.

FIG. 3 is a detailed view of exchangeable moisture detector 5 for women and soiling, double-side adhesive foam body 7, pair of metal wires 8, layer of gauze 9, electric wire 5a connecting plastic box 4 with exchangeable moisture detector, and coupling 5b connecting exchangeable moisture detector 5 with electric wire 5a.

Figure 4:
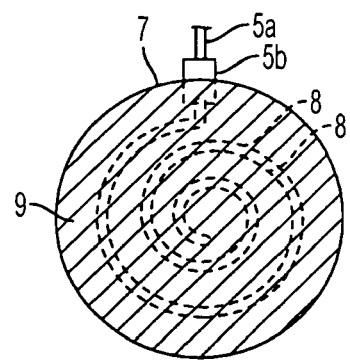
FIG. 4 is a detailed view of exchangeable moisture detector for men.

FIG. 4 is a detailed view of exchangeable moisture detector 5 for men, double-side adhesive foam body 7, pair of metal wires 8, layer of gauze 9, electric wire 5a connecting plastic box 4 with the exchangeable moisture detector, coupling 5b connecting exchangeable moisture detector 5 with electric wire 5a.

Figure 5:
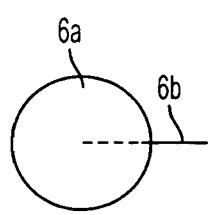
FIG. 5 is a front view of wetting-stopping and arousing signals application unit.

FIG. 5 is a front view of wetting-stopping and arousing signals application unit 6, round metal plate 6a, electric wire 6b connecting plastic box 4 with wetting-stopping and arousing signals application unit 6.

Figure 6:
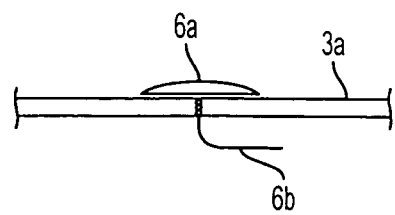
FIG. 6 is a side view of a wetting-stopping and arousing signals application unit.

FIG. 6 is a side view of wetting-stopping and arousing signals application unit 6, round metal plate 6a, electric wire 6b connecting plastic box 4 with wetting-stopping and arousing signals application unit 6.

Before use, fast-acting counter-incontinency device 3 has to be pre-adjusted to the individual sensitivity of the person according to the flowchart of FIG. 7.

If the first treatment with the device does not cease in a split second the incontinent release of biological fluids and does not arouse the patient immediately, the number of the electrical signals has to be increased by regulator 4e on plastic box 4. The strength of the signals can be increased also until reaching the necessary effect by regulator 4b.

Steps of actual application of the pre-adjusted fast-acting counter-incontinence device 3 comprise:

a. attaching pre-adjusted fast-acting counter-incontinence device 3 by belt 3a to the lower part of the abdomen 1 of the person by hook-and-loop fastener 3b;

b. connecting moisture detector 5 with plastic box with power source and microprocessor electronics 4 by electric wire 5a and coupling 5b;

c. fixing moisture detector 5 under a person's briefs, panties or diaper where wetness would first appear by the rear side of double-side adhesive foam body 7;

d. turning device 3 on by on/off switch 4c;

e. device 3 remains in stand-by position until the first drops of involuntary released liquid moisten layer of gauze 9 and pair of metal wires 8 which adhere to one side of double-adhesive foam body 7 of moisture detector 5 making electrical contact between pair of metal wires 8;

f. this activates the microprocessor electronics 4b powered by power source 4a in plastic box 4 to release immediately the pre-programmed series of wetting-stopping and arousing signals application units 6 and are applied to the lower part of the person's abdomen 1 by pair of round plates 6a;

g. after releasing the preset series of wetting-stopping and arousing signals device 3 automatically returns to stand-by position; and h. preparing device 3 for the next application by replacing the wetted moisture detector 5.

The method of the invention is a based on two principles:

a. the establishment of behavioral conditioning requires a fully awake brain; and b. conditioned reflexes are permanent if established during the 2-3 seconds phasic period of the response time to a signal. Such reflexes are very resistive to habituation. (Habituation is an organism's tendency of learning not to transfer or not to respond to sensory information.) The reflexes developed during the more prolonged tonic reaction time, which follows the phasic reaction time and lasts several minutes, typical of prior art methods, habituate easily and require a considerably longer time to be acquired.

Therefore, the method of the invention is based on two nerve mechanisms caused provided by a series of electrical signals pre-adjusted to the individual sensitivity of the person.

A first signal causes an instant cessation of the involuntary release of biological fluids by a simple reflex, without participation of the brain. Simultaneously, it arouses the brain in a split second after the beginning of the wetting. Further signals meet an already aroused brain, able to consciously connect the involuntary wetting with the arousing signal. The appearance of the whole series of electrical signals in the 2 to 3 seconds phasic period causes a fast building up of a durable aversive conditioned reflex, i.e. a conditioning by linking an unpleasant stimulus with the performance of an undesirable behavior. This programs the brain in establishing a proper brain control on the bladder or anal sphincter.

Experimental results have confirmed these physiological mechanisms. They lead to a speedy acquisition of the proper brain control of the sphincters by means of aversive conditioning, unutilized by the methods mentioned in the "Discussion of Related Art" section.

The main advantage of the method and device of the invention is the short time for the establishment of proper brain control on bladder and anal sphincters respectively from many months of treating to a few applications at most, as described in the section "Physiological Mechanisms of the Method".

The short time span between the start of involuntary wetting or soiling and its cessation, typically a split second, not only speeds up the acquisition of the proper reflex, but also eliminates further worsening of the situation, thereby preserving the self-esteem of the person.

Also, there is no need to awaken parents and guardians to perform arousal, as recommended by other devices.

The invented method also makes unnecessary the person's awakening by parents or guardians.

The soundless nature of the electric wetting-stopping and arousing signals preserves the privacy of the involuntary bed-wetting or soiling person, thus making the method and device useful in the presence of other people, like in school, camps, and other public places. The use of the device would not be apparent to other people present. This quality makes the method and device applicable not only for the elimination of nighttime, but also daytime, wetting as well as soiling.

The invention claimed is:

1. A fast-acting counter-incontinence device for elimination of involuntary wetting and soiling in a person by building up the necessary behavioral conditioning for proper brain control of bladder and anal sphincter after a few applications, said device comprising:

a package, said package comprising
    a power source,
    microprocessor electronics adapted to produce a series of electrical signals
    an on/off switch, and
    a regulator regulating a strength of said electrical signals,
means for holding said package around the lower abdomen of the person
a pair of said electrical signals application units, adapted to be applied to the lower part of the person's abdomen,
electrical connection means connecting said package with said pair of electrical signals application units,
an exchangeable moisture detector, said moisture detector being adapted to be positioned in proximity to the person's urethral or anal tract opening,
electrical means coupling said exchangeable moisture detector to said package
whereby wetting causes said moisture detector to activate said microprocessor electronics to generate electrical signals of pre-programmed strength and number for transmittal by said pair of application units to said person's lower abdomen, comprising: (1) a first arousing electrical signal causing an instant cessation of wetting through stimulation of a simple reflex, without the participation of the brain while simultaneously arousing the brain coinciding with the beginning of the wetting and; (2) a further at least one subsequent electrical signal to the aroused brain at a time interval effective to connect the involuntary wetting with the subsequent electrical signal causing a fast build up of a durable aversive conditioned reflex to wetting by linking an unpleasant stimulus with the performance of the undesirable behavior of wetting.

2. The device of claim 1 wherein said moisture detector comprises a double-adhesive foam body covered on one side by a layer of gauze which encapsulates a pair of metal wires each connected to said coupling at one extremity and separated by a gap at another extremity, whereby moistening of said layer of gauze by biological fluids provides an electric contact across said gap.

3. A method for elimination of involuntary wetting and soiling of a person by use of a fast-acting counter-incontinence device comprising a belt fastened around a lower abdomen of the person by a hook-and-loop fastener; a plastic box attached to said belt, said plastic box containing a power source, microprocessor electronics producing wetting-stopping and arousing signals, an on/off switch, a regulator regulating a strength of said signals, a regulator for pre-programming a number of said signals; further a pair of wetting-stopping and arousing signals application units, a pair of connecting wires connecting said plastic box with said pair of wetting-stopping and arousing signals application units, a connecting electric wire attached at its one extremity to said plastic box and by its other extremity with a coupling, said coupling attached at its one extremity to another extremity of said electric wire; and an exchangeable moisture detector attached to another extremity of said coupling; said method comprising the steps of:

a. fastening a combination of said belt, said plastic box, said pair of wetting-stopping and arousing signals application units, and said pair of electric wires connecting plastic box with pair of wetting stopping and arousing signals application units around a lower abdomen of the person;
b. turning on said on/off switch;
c. connecting said electric wire to said coupling;
d. placing said moisture detector in an undergarment of the person;
e. connecting said coupling to said moisture detector, thereby closing an electric circuit and activating said device;
f. gradually increasing a strength of said signals by said strength regulator and applying said signals to the person through said application units until the person experiences the sensation of a pinprick, constituting a pre-set signals strength;
g. pre-programming a number of said signals by said number regulator;

whereby steps a. through g. accomplish pre-adjustment of said device, and whereby any involuntary wetting again closes said electric circuit to activate said device to apply said pre-programmed number of said signals of said pre-set strength through said application units to the person to eliminate involuntary wetting by the person; and h. replacing used said exchangeable moisture detector with a dry one for a subsequent application.

4. The device of claim 1 where said package further comprises said regulator for pre-programming a number of said signals.

* * * * *